United States Patent [19]

Arndt et al.

[11] 4,159,902
[45] Jul. 3, 1979

[54] 1,3,3-TRIMETHYL-6-AZABICYCLO-(3.2.1)-OCTANE-6-CARBOXYLIC ACID ESTER, HERBICIDES, PROCESS FOR MAKING SAME AND COMPOSITION CONTAINING SAME

[75] Inventors: Friedrich Arndt; Ludwig Nüsslein, both of Berlin, Fed. Rep. of Germany

[73] Assignee: Schering Aktiengesellschaft, Berlin and Bergkamen, Fed. Rep. of Germany

[21] Appl. No.: 819,415

[22] Filed: Jul. 26, 1977

[51] Int. Cl.² .................... C07D 209/02; A01N 9/22
[52] U.S. Cl. .................... 71/95; 260/376.32; 260/326.82
[58] Field of Search .......... 260/326.32, 326.82; 71/95, 88

[56] References Cited

U.S. PATENT DOCUMENTS

| | | |
|---|---|---|
| 3,198,786 | 8/1965 | Tilles et al. ............................ 71/88 |
| 3,344,134 | 9/1967 | D'Amico ................................ 71/88 |
| 3,705,165 | 12/1972 | Sturm et al. .................... 260/326.32 |
| 3,820,974 | 6/1974 | Sturm et al. ............................ 71/95 |
| 3,839,337 | 10/1974 | Sturm et al. ............................ 71/95 |
| 3,872,126 | 3/1975 | Sturm et al. ............................ 71/95 |

OTHER PUBLICATIONS

Edwards et al., Chem. Abs., vol. 81: 104267f (1974).
Krow et al., Chem. Abs., vol. 81: 105237h (1974).
Schneider, Chem. Abs., vol. 76: 14312j (1972).
Snyder et al., Chem. Abs., vol. 34: 996⁴ (1939).
Hewgill et al.; Chem. Abs., vol. 50: 7730i (1956).
Sturm et al., Chem. Abs., vol. 74: 99910j (1971).
Pellacani et al., J. Org. Chem., vol. 41, pp. 1282–1283 (1976).
Kuehne et al., J. Org. Chem., vol. 40, pp. 1287–1291 (1975).

*Primary Examiner*—Donald G. Daus
*Assistant Examiner*—Mary C. Lee
*Attorney, Agent, or Firm*—Michael J. Striker

[57] ABSTRACT

1,3,3-trimethyl-6-azabicyclo-(3.2.1)-octane-6-carboxylic acid ester of the formula

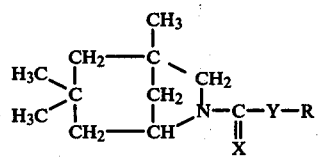

in which R is an aliphatic hydrocarbon residue which may also be substituted, a cycloaliphatic hydrocarbon residue which may also be substituted, an aromatic hydrocarbon residue which may also be substituted or an araliphatic hydrocarbon residue and wherein X and Y are oxygen or sulphur. The compounds of the invention are characterized by a superior herbicidal activity in particular against monocotyl weeds. They also have excellent selective properties for agricultural plants.

The invention also embraces a process of making the compounds of the invention and compositions in which the compounds of the invention form at least one of the active components.

18 Claims, No Drawings

4,159,902

1,3,3-TRIMETHYL-6-AZABICYCLO-(3.2.1)-OCTANE-6-CARBOXYLIC ACID ESTER, HERBICIDES, PROCESS FOR MAKING SAME AND COMPOSITION CONTAINING SAME

BACKGROUND OF THE INVENTION

The invention relates to novel 1,3,3-trimethyl-6-azabicyclo-(3.2.1)-octane-6-carboxylic acid esters.

The herbicidal activity of alkyleneimocarbothiolates is known (U.S. Pat. No. 3,198,786). These compounds, however, have a sufficient selective-herbicidal activity only in specific agricultural plantations, such for instance as in rice cultures where they can be used to combat Echinochloa spp.

It is therefore an object of the present invention to provide a compound of this type which has a broad selectivity as to a large number of agricultural plants together with a high herbicidal activity against weeds.

SUMMARY OF THE INVENTION

This object is solved by a herbicide formed by a 1,3,3-trimethyl-6-azabicyclo-(3.2.1)-octane-6-carboxylic acid ester which has the formula

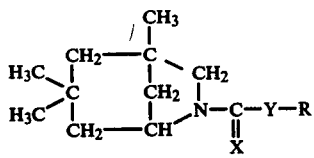

in which R is an aliphatic hydrocarbon residue which may also be substituted, a cycloaliphatic hydrocarbon residue which may also be substituted, an aromatic hydrocarbon residue which may also be substituted or an araliphatic hydrocarbon residue and wherein X and Y are oxygen or sulphur.

The compounds of the invention are characterized by a superior herbicidal activity particularly against monocotyl weeds, for instance Avena, Alopecurus, Echinochloa c.g., Setaria, Digitaria, Poa, Hordeum and Triticum.

Because of their excellent selectivity the compounds can be used in agricultural plantations, for instance in fields where cauliflower, sugar beets, seed-tomatoes, bush beans, cotton and rice are grown.

The compounds of the invention furthermore can also be used in maize and sorghum plantations in which case preferably antiodotes such as 8-naphthalic acid anhydride or N,N-diallylchloroacetamide are added to the seed or to the sprayed mass of active agents.

A further advantage of the compounds of the invention is that they also have growth controlling properties. The compounds of the invention have a satisfactory effect already in amounts starting with 1 kg of active agent per about 2.5 acres of ground and because of their surprisingly broad spectrum of selectivity they can be used in amounts up to 8 kg of active agent per about 2.5 acres prior to the seed by implantation in the ground without damage to the agricultural plants.

The compounds of the invention can either be used alone or intermixed with each other or in mixture with other different active agents.

DISCUSSION OF THE INVENTION AND PREFERRED EMBODIMENTS

Depending on the desired purpose the following additional herbicidal agents may for instance be used and may also be added only immediately prior to use of the compounds of the invention:

substituted anilines,
substituted aryloxycarboxylic acids and their salts, esters and amides,
substituted ethers,
substituted arsonic acids and their salts, esters and amides,
substituted benzimidazoles,
substituted benzisothiazoles,
substituted benzthiadiazinone dioxides,
substituted benzoxazines,
substituted benzoxazinones,
substituted benzthiazoles,
substituted benzothiadiazines,
substituted biurets,
substituted quinolines,
substituted carbamates,
substituted aliphatic carboxylic acids and their salts, esters and amides,
substituted aromatic carboxylic acids and their salts, esters and amides,
substituted carbamoylalkyl-thio- or dithiophosphates.
substituted quinazolines,
substituted cycloalkylamidocarbonylthiol acids and their salts, esters and amides,
substituted cycloalkylcarbonylamido-thiazoles,
substituted dicarboxylic acids and their salts, esters and amides,
substituted dihydrobenzofuranylsulfonates,
substituted disulfides,
substituted dipyridylium salts,
substituted dithiocarbamates,
substituted dithiophosphoric acids and their salts, esters and amides,
substituted urea derivatives,
substituted hexahydro-1H-carbothioates,
substituted hydantoines,
substituted hydrazides,
substituted hydrazonium salts,
substituted isoxazolpyrimidones,
substituted imidazoles,
substituted isothiazolpyrimidones,
substituted ketones,
substituted naphthoquinones,
substituted aliphatic nitriles,
substituted aromatic nitriles,
substituted oxadiazoles,
substituted oxadiazinons,
substituted oxadiazolidinediones,
substituted oxadiazinediones,
substituted phenols and their salts and esters,
substituted phosphonic acids and their salts, esters and amides,
substituted phosphoniumchlorides,
substituted phosphonalkylglycines,
substituted phosphites,
substituted phosphoric acids and their salts, ester and amides,
substituted piperidines,
substituted pyrazoles, substituted pyrazolalkylcarboxylic acids and their salts, esters, and amides,
substituted pyrazolium salts,
substituted pyrazoliumalkylsulfates,
substituted pyridazines,
substituted pyridazones
substituted pyridine-carboxylic acids and their salts, esters and amides,
substituted pyridines,
substituted pyridinecarboxylates,
substituted pyridinone,
substituted pyrimidone,
substituted pyrrolidine-carboxylic acids and their salts, esters and amides,
substituted pyrrolidines,
substituted arylsulfonic acids and their salts, esters and amides,
substituted styrenes,
substituted tetrahydro-oxadiazinediones,
substituted tetrahydromethanoindenes,
substituted tetrahydro-diazol-thiones,
substituted tetrahydro-thiadiazine-thiones,
substituted tetrahydro-thiadiazolediones,
substituted thiadiazoles,
substituted aromatic thiocarboxylic acid amides,
substituted thiocarboxylic acids and their salts, esters and amides,
substituted thiolcarbamates,
substituted thiophosphoric acids and their salts, esters and amides,
substituted triazines,
substituted triazoles
substituted uracils, and
substituted urethidindiones.

In addition other additives may also be used such as for instance nonphytotoxic additives which result in a synergistic increase of the activity in herbicides such as wetting agents, emulsifiers, solvents and oily additives.

The compounds of the invention or their mixtures are preferably used in the form of powders, dusting agents, granulates, solvents, emulsions or suspensions to which may be added liquid and/or solid carrier materials or diluents and, if desired, agents which improve the wetting, adhesion, emulsifying and/or dispersion properties.

Suitable liquid carrier materials are for instance water, aliphatic and aromatic hydrocarbons, such as, benzene, toluene, xylene, cyclohexanone, isophorone, dimethylsulfoxide, dimethylformamide, and furthermore mineral oil fractions.

Solid carrier materials are mineral earths, for instance, tonsil, silica gel, talc, kaolin, attaclay, limestone, silicic acid and plant products, for instance flours.

There may also be added surface active agents, for instance, calciumlignosulfonate, polyoxyethylene alkylphenylethers, naphthaline sulfonic acids and their salts, phenolsulfonic acids and their salts, formaldehyde condensation products, fatty alcohol sulfates as well as substituted benzosulfonic acids and their salts. The amount of the active agent or agents can be varied widely. The compositions may for instance contain the active agents in an amount of about 10 to 80% by weight, together with about 90 to 20% by weight of liquid or solid carrier materials and, if desired, up to 20% by weight of surface active agents.

The application of the agents can be effected in conventional form. They may for instance be applied with water as carrier material in spray amounts of about 100 to 1000 liter per 2.5 acres. An application of the agents is possible in the so-called "low-volume" and "ultra low-volume" process as well as in the form of so-called microgranulates. Among the compounds of the invention those are particularly preferred in which in the above formula R is alkyl of 1 to 7 carbon atoms, chloroalkyl of 1 to 7 carbon atoms, alkenyl of 2 to 7 carbon atoms, chloroalkenyl of 2 to 7 carbon atoms, alkinyl of 2 to 7 carbon atoms, benzyl or chlorobenzyl, phenyl or naphthyl, chlorophenyl, alkylphenyl wherein the alkyl moieity has 1 to 4 carbon atoms, chloroalkylphenyl wherein allyl has again 1 to 4 carbon atoms and in which compounds X and Y are oxygen or sulphur.

Among the radicals identified as R in the proceeding paragraph the following are preferred: methyl, ethyl, 2-chloroethyl, propyl, isopropyl, allyl, 2-propinyl, dichloroallyl, trichloroallyl, butyl, sec.-butyl, isobutyl, tert.-butyl, butenyl, butinyl, pentyl, isopentyl, benzyl, 4-chlorobenzyl, 2,4-dichlorobenzyl, phenyl, 4-chlorophenyl and many others.

The compounds which have so far not been described in the literature can be made in different ways.

I. 1,3,3-trimethyl-6-azabicyclo-(3.2.1)-octane of the formula

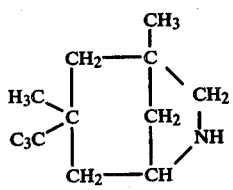

which may be dissolved in a solvent are reacted with halogenated formic acid esters of the formula

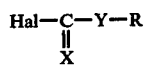

which reaction may be effected in the presence of an acid acceptor. Hal is halogen and R, Y and X have the meaning as in the above formula of the final compound.

II. 1,3,3-trimethyl-6-azabicyclo-(3.2.1)-octane of the formula

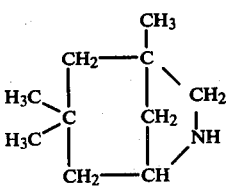

which may be dissolved in a solvent may also be reacted with a compound of the formula

in the presence of a base B so as to form the salt of the base having the formula

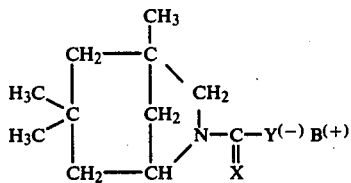

wherein the salt is treated with an alkylating agent R—Z. R, Y and X have the meaning as in the above formula, B has been identified above as a base and Z is a halogen or alkyl- or toluene sulfphuric acid residue.

III. 1,3,3-trimethyl-6-azabicyclo-(3.2.1)-octane of the formula

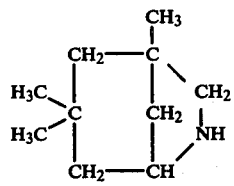

which may be dissolved in a solvent may be reacted with a phosgene compound of the formula Hal$_2$C=X so as to form
1,3,3-trimethyl-6-azabicyclo-(3.2.1)-octane-6-carboxylic acid halide of the formula

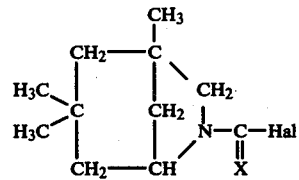

The thus obtained reaction product is then caused to react with an oxygen- or thio compound of the formula

R—Y$^{(-)}$B$^{(+)}$

R, S and Y in these formulae have again the meaning as in the above formula of the final product and Hal indicates a halogen or an alkyl sulphuric acid residue or a toluene sulfonic acid residue.

As bases or acid acceptors in the above reactions can be used all conventional proton acceptors. For this purpose organic bases may be used, such as, tertiary amines like triethylamine or N,N-dimethylaniline or a pyridine base; furthermore, suitable inorganic bases, such as, oxides, hydroxides and carbonates of the alkali and alkaline-earth metals. Liquid bases can at the same time function as solvents. An excess of the employed initial liquid base may form also the acid acceptor.

As alkylation agents, preferably chlorides, bromides and iodides are used.

The reaction of the individual components can be effected at a temperature between about 0° and 120° C. preferably, however, at room temperature.

The components are preferably used in about equimolar amounts.

Suitable reaction media should be inert towards the reactants as solvents, either alone or when used in mixture with water. The following may be named: aliphatic and aromatic hydrocarbons, such as petroleum ether, cyclohexane, benzene, toluene and xylene; halogenated hydrocarbons such as methylene chloride, chloroform, carbontetrachloride; halogenated ethylenes; ether-type compounds such as diethylether, diisopropylether, tetrahydrofuran, and dioxane, ketones, such as acetone, methylisobutylketone and isophorone; ester, such as acetic acid methyl- and ethylester; acid amides, like dimethylformamide and hexamethylphosphoric acid triamide, carboxylic acid nitrile, like acetonitrile and many others. The isolation of the compounds of the invention is effected at the end of the reaction by distilling off the solvent or extractive agent at normal or reduced pressure. If desired, the reaction product may, prior to isolation, be treated with an acid or basic agent in order to remove undesirable byproducts. If necessary the compounds can be distilled in a vacuum in order to obtain them in high purity.

The following examples will further illustrate the making of the compounds of the invention.

EXAMPLE 1

24.9 of chlorothioformic acid-S-ethylester were slowly added dropwise at room temperature and while stirring to a solution of 61.3 g 1,3,3-trimethyl-6-azabicyclo-(3.2.1)-octane in 150 ml diisopropylether. After stirring for one hour the reaction mixture was shaken with water, then with dilute hydrochloric acid and afterwards again with water. The organic phase was dried on magnesium sulfate, the solvent was distilled off in a vacuum and residual solvent was finally removed in a high vacuum.

By reacting the first-obtained water extract with sodium hydroxide the excess of starting product was recovered.

Yield: 46.0 g (95.29% of the theoretical value) of 1,3,3-trimethyl-6-azabicyclo-(3.2.1)-octane-6-thiocarboxylic acid-S-ethylester; $n_D^{20}=1.5123$.

Analysis: calculated: C 64.68%, H 9.60%, N 5.80%. obtained: C 64.38%, H 9.65%, N 6.01%.

EXAMPLE 2

15.2 g of carbondisulfide were added dropwise while stirring at a temperature between 10° and 15° C. to a mixture of 34 ml 1,3,3-trimethyl-6-azabicyclo-(3.2.1)-octane, 50 ml acetonitrile and 8 g of sodium hydroxide dissolved in 50 ml water. Stirring was then continued for 2 hours to obtain the dithiocarbamic acid salt. Thereafter 24.5 g of allylbromide were added dropwise to the reaction mixture and stirring was continued for 1 hour to cause formation of the ester. After adding 500 ml methylene chloride the organic phase was shaken with dilute hydrochloric acid, dried on magnesium sulfate, treated with activated carbon and concentrated by evaporation in a high vacuum.

There were obtained 52 g (96.4% of the theoretical value) of 1,3,3-trimethyl-6-azabicyclo-(3.2.1)-octane-6-dithiocarboxylic acid allylester; $n_D^{20}=1.5810$.

Analysis: calculated: C 62.40%, H 8.60%, N 5.20%, S 23.80%, obtained: C 62.23%, H 8.53%, N 5.02%, S 23.71%.

EXAMPLE 3

5.4 g of sodiumethylate were added while stirring to a solution of 21.5 g of 1,3,3-trimethyl-6-azabicyclo-(3.2.1)-octane-6-carboxylic acid chloride in 100 ml acetonitrile. After stirring for 2 hours the reaction mixture was reacted with 350 ml water. The separated oil was then extracted with chloroform and the chloroform phase was shaken with dilute hydrochloric acid followed by drying on magnesium sulfite and finally distilling off of the solvent in a high vacuum.

There were obtained 19.0 g (90.2% of the theoretical value) of the oily product constituted by 1,3,3-trimethyl-6-azabicyclo-(3.2.1)-octane-6-carboxylic acid methylester; $n_D^{20} = 1.4840$.

Analysis: calculated: C 68.21%, H 10.02%, N 6.63%. obtained: C 68.23%, H 10.01%, N 7.03%.

In an analogous manner the following compounds of the invention were prepared.

| Compound | Physical constants |
|---|---|
| 1,3,3-trimethyl-6-azabicyclo-(3.2.1)-octane-6-thiocarboxylic acid-S-methyl-ester | $n_D^{20} = 1.5172$ |
| 1,3,3-trimethyl-6-azabicyclo-(3.2.1)-octane-6-thiocarboxylic acid-S-propyl-ester | $n_D^{20} = 1.5090$ |
| 1,3,3-trimethyl-6-azabicyclo-(3.2.1)-octane-6-thiocarboxylic acid-S-benzyl-ester | $n_D^{20} = 1.5526$ |
| 1,3,3-trimethyl-6-azabicyclo-(3.2.1)-octane-6-carboxylic acid-ethylester | $n_D^{20} = 1.4702$ |
| 1,3,3-trimethyl-6-azabicyclo-(3.2.1)-octane-6-carboxylic acid-propylester | $n_D^{20} = 1.4692$ |
| 1,3,-trimethyl-6-azabicyclo-(3.2.1)-octane-6-carboxylic acid-butylester | $n_D^{20} = 1.4612$ |
| 1,3,3-trimethyl-6-azabicyclo-(3.2.1)-octane-6-carboxylic acid-isopropylester | $n_D^{20} = 1.4652$ |
| 1,3,3-trimethy-6-azabicyclo-(3.2.1)-octane-6-carboxylic acid-(2-propenyl)-ester | $n_D^{20} = 0\ 1.4796$ |
| 1,3,3-trimethyl-6-azabicyclo-(3.2.1)-octane-6-carboxylic acid-phenylester | $n_D^{20} = 1.5224$ |
| 1,3,3-trimethyl-6-azabicyclo-(3.(3.2.1)-octane-6-thiocarboxylic acid-S-(4-fluorophenyl)ester | $n_D^{20} = 0\ 1.5488$ |
| 1,3,3-trimethyl-6-azabicyclo-(3.(3.2.1)-octane-6-carboxylic acid-benzylester | $n_D^{20} = 1.5212$ |
| 1,3,3-trimethyl-6-azabicyclo-(3.2.1)-octane-6-carboxylic acid-pentylester | $n_D^{20} = 1.4664$ |

The compounds of the invention are colorless or slightly yellowish oils which have a faint aromatic smell and which are insoluble in water but have good solubility in all organic solvents, for instance in hydrocarbons, halogenated hydrocarbons, ethers, ketones, carboxylic acid esters, carboxylic acid amides, carboxylic acid nitriles, alcohols, carboxylic acids, sulfoxides and many others.

USES AND ACTIVITY

The following examples will illustrate the application of the compound of the invention and its activity.

EXAMPLE 4

The compounds listed below in Table I were applied in a hothouse in an amount of 5 kg of active agent per 2.5 acres suspended in 500 liter water per 2.5 acres. The application was effected by spraying the material onto the ground prior to seeding and working it into the ground whereupon Lolium and Setaria were then grown on the thus treated ground. Three weeks after treatment the results were evaluated on a scale from 0==no effect to 4=total destruction of the plants.

TABLE I

| Compounds of the Invention | Lolium | Setaria |
|---|---|---|
| 1,3,3-trimethyl-6-azabicyclo-(3.2.1)-octane-6-thiocarboxylic acid-S-ethyl-ester | 4 | 4 |
| 1,3,3-trimethyl-6-azabicyclo-(3.2.1)-octane-6-thiocarboxylic acid-S-methyl-ester | 4 | 4 |
| 1,3,3-trimethyl-6-azabicyclo-(3.2.1)-octane-6-thiocarboxylic acid-S-propyl-ester | 4 | 4 |
| octane-6-dithiocarboxylic acid-(2-propenyl)-ester | 4 | 3 |
| 1,3,3-trimethyl-6-azabicyclo-(3.2.1)-octane-6-thiocarboxylic acid-S-benzylester | 3 | — |

Analogous activity had:

1,3,3-trimethyl-6-azabicyclo-(3.2.1)-octane-6-carboxylic acid-methylester
1,3,3-trimethyl-6-azabicyclo-(3.2.1)-octane-6-carboxylic acid ethylester
1,3,3-trimethyl-6-azabicyclo-(3.2.1)-octane-acid propylester
1,3,3-trimethyl-6-azabicyclo-(3.2.1)-octane-acid butylester
1,3,3-trimethyl-6-azabicyclo-(3.2.1)-octane-6-carboxylic acid isopropylester
1,3,3-trimethyl-6-azabicyclo-(3.2.1)-octane-6-carboxylic acid-(2-propenyl)-ester
1,3,3-trimethyl-6-azabicyclo(3.2.1)-octane-6-carboxylic acid phenylester
1,3,3-trimethy-6-azabicyclo-(3.2.1)-octane-6-carboxylic)acid-S-(4-fluorophenyl)-ester Analogous activity had:

1,3,3-trimethyl-6-azabicyclo-(3.2.1)-octane-6-carboxylic acid-methylester 1,3,3-trimethyl-6-azabicyclo-(3.2.1)-octane-6-carboxylic acid ethylester 1,3,3-trimethyl-6-azabicyclo-(3.2.1)-octane-6-carboxylic acid propylester 1,3,3-trimethyl-6-azabicyclo-(3.2.1)-octane-6-carboxylic acid butylester 1,3,3-trimethyl-6-azabicyclo-(3.2.1)-octane-6-carboxylic acid isopropylester 1,3,3-trimethyl-6-azabicyclo-(3.2.1)-octane-6-carboxylic acid-(2-propenyl)-ester 1,3,3-trimethyl-6-azabicyclo-(3.2.1)-octane-6carboxylic acid phenylester 1,3,3-trimethyl-6-azabicyclo-(3.2.1)-octane-6-thiocarboxylic acid-S-(4-fluorophenyl)-ester 1,3,3-trimethyl-6-azabicyclo-(3.2.1)-octane-6-carboxylic acid benzylester 1,3,3-trimethyl-6-azabicyclo-(3.2.1)-octane-6-carboxylic acid pentylester

EXAMPLE 5

The plants listed below in Table II were treated in a preemergence application in a hothouse with the compounds listed in the Table in amounts of 3 kg of active agent per about 2.5 acres. The agents were applied to the ground in a uniform manner as an aqueous dispersion in 500 liter per about 2.5 acres and the dispersion was subsequently worked into the ground. The results obtained 3 weeks after treatment show that the compound of the invention are superior to the comparison material.

TABLE II

| Compound of the Invention | 3 kg/about 2.5 acres | cotton | soy-beans | rice | Trit-icum | Hordeum | Avena | Alope-curus | Echino-chloa | Set-aria | Digi-taria | Poa |
|---|---|---|---|---|---|---|---|---|---|---|---|---|
| 1,3,3-trimethyl-6-azabicyclo-(3.2.1)-octane-6-thiocarboxylic acid-S-ethylester | 3 | 10 | 10 | 10 | 0 | 0 | 0 | 0 | 0 | 0 | 0 | 0 |
| Comparison Compound (Pat. 3,198,786) S-ethyl-N,N-hexamethylenethio-carbamate | | 0 | 3 | 10 | 10 | 10 | 0 | 0 | 0 | 3 | 3 | 0 |
| Untreated | | 10 | 10 | 10 | 10 | 10 | 10 | 10 | 10 | 10 | 10 | 10 |

0 = total destruction
10 = no injury to plants

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. 1,3,3-trimethyl-6-azabicyclo-(3.2.1)-octane-6-carboxylic acid ester of the formula

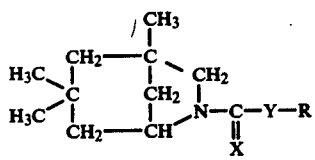

in which R is alkyl of 1 to 7 carbon atoms, chloro-alkyl of 1 to 7 carbon atoms, alkenyl of 2 to 7 carbon atoms, chloroalkenyl of 2 to 7 carbon atoms, alkinyl of 2 to 7 carbon atoms, benzyl, chlorobenzyl, phenyl, naphthyl, chlorophenyl, alkylphenyl having 1 to 4 carbon atoms in the alkyl moiety of chloroalkylphenyl having again 1 to 4 carbon atoms in the alkyl portion and wherein X and Y are oxygen or sulphur.

2. The compound of claim 1 which is 1,3,3-trimethyl-6-azabicyclo-(3.2.1)-octane-6-thiocarboxylic acid-S-ethylester.

3. The compound of claim 1 which is 1,3,3-trimethyl-6-azabicyclo-(3.2.1)-octane-6-dithiocarboxylic acid-2-(propenyl)-ester.

4. The compound of claim 1 which is 1,3,3-trimethyl-6-azabicyclo-(3.2.1)-octane-6-thiocarboxylic acid-S-methylester.

5. The compound of claim 1 which is 1,3,3-trimethyl-6-azabicyclo-(3.2.1)-octane-6-thiocarboxylic acid-S-propylester.

6. The compound of claim 1 which is 1,3,3-trimethyl-6-azabicyclo-(3.2.1)-octane-6-thiocarboxylic acid-S-benzylester.

7. The compound of claim 1 which is 1,3,3-trimethyl-6-azabicyclo-(3.2.1)-octane-6-carboxylic acid methylester.

8. The compound of claim 1 which is 1,3,3-trimethyl-6-azabicyclo-(3.2.1)-octane-6-carboxylic acid ethylester.

9. The compound of claim 1 which is 1,3,3-trimethyl-6-azabicyclo-(3.2.1)-octane-6-carboxylic acid propylester.

10. The compound of claim 1 which is 1,3,3-trimethyl-6-azabicyclo-(3.2.1)-octane-6-carboxylic acid butylester.

11. The compound of claim 1 which is 1,3,3-trimethyl-6-azabicyclo-(3.2.1)-octane-6-carboxylic acid isopropylester.

12. The compound of claim 1 which is 1,3,3-trimethyl-6-azabicyclo-(3.2.1)-octane-6-carboxylic acid-(2-propenyl)-ester.

13. The compound of claim 1 which is 1,3,3-trimethyl-6-azabicyclo-(3.2.1)-octane-6-carboxylic acid phenylester.

14. The compound of claim 1 which is 1,3,3-trimethyl-6-azabicyclo-(3.2.1)-octane-6-thiocarboxylic acid-S-(4-fluorophenyl)-ester.

15. The compound of claim 1 which is 1,3,3-trimethyl-6-azabicyclo-(3.2.1)-octane-6-carboxylic acid benzylester.

16. The compound of claim 1 which is 1,3,3-trimethyl-6-azabicyclo-(3.2.1)-octane-6-carboxylic acid pentylester.

17. A herbicidal composition comprising at least one active agent as defined in claim 1 in an amount from about 10 to 80% by weight and a liquid or solid carrier material in an amount of about 90 to 20% by weight.

18. The composition of claim 17 which includes up to about 20% by weight of a surface active agent or agents.

* * * * *